(12) United States Patent
Istook

(10) Patent No.: US 6,341,504 B1
(45) Date of Patent: Jan. 29, 2002

(54) COMPOSITE ELASTIC AND WIRE FABRIC FOR PHYSIOLOGICAL MONITORING APPAREL

(75) Inventor: Cynthia L Istook, Raleigh, NC (US)

(73) Assignee: VivoMetrics, Inc., Ventura, CA (US)

( * ) Notice: Subject to any disclaimer, the term of this patent is extended or adjusted under 35 U.S.C. 154(b) by 0 days.

(21) Appl. No.: 09/774,333

(22) Filed: Jan. 31, 2001

(51) Int. Cl.⁷ .............................. A61B 5/04; D04B 1/00
(52) U.S. Cl. .................. 66/172 E; 66/171; 66/202; 2/69; 600/388
(58) Field of Search .................. 66/169 R, 170, 66/171, 172 E, 190, 191, 192, 193, 202; 2/69, 76, 167, 902, 901; 600/386, 390, 391

(56) References Cited

U.S. PATENT DOCUMENTS

| | | | | |
|---|---|---|---|---|
| 4,753,088 A | * | 6/1988 | Harrison et al. | 66/202 |
| 5,074,129 A | * | 12/1991 | Matthew | 66/193 |
| 5,416,961 A | * | 5/1995 | Vinay | 66/190 |
| 5,991,922 A | * | 11/1999 | Banks | 2/69 |
| 6,047,203 A | * | 4/2000 | Sackner et al. | 600/386 |
| 6,066,093 A | * | 5/2000 | Kelly et al. | 600/386 |

\* cited by examiner

*Primary Examiner*—Danny Worrell
(74) *Attorney, Agent, or Firm*—Pennie & Edmonds LLP

(57) ABSTRACT

A fabric for use in apparel of the type used for physiological monitoring of prescribed body functions has one or more elongated bands of elastic material which is stretchable in the longitudinal direction. Each such elastic band includes at least one conductive wire affixed to or formed therein in a curved pattern. A garment and a system of the type used for physiological monitoring of prescribed body functions includes such a fabric and a monitoring unit monitoring electrical parameters of the included conductive wires.

9 Claims, 10 Drawing Sheets

| | |
|---|---|
| BAR 1 | 4 ENDS 1/150 SD |
| BAR 2 | 12 ENDS 1680 GLOSPAN |
| BAR 3 | 2 ENDS 1/150 SD |
| BAR 4 | 1 END NE 12544 TR TINNED COPPER WIRE |
| BAR 5 | |
| BAR 6 | |
| BAR 7 | |
| BAR 8 | |
| WARPS | 12 ENDS 1/150 SD |
| | |
| NEEDLES - WIDTH | 12-3/4" |
| STRETCH AT KNITTER | 110+/-10% |
| STRETCH AFTER 2 HOURS | |
| STRETCH AFTER CALENDAR | N/C |
| FRONT PICKS | 19 |
| BACK PICKS AT KNITTER | 40 |
| BACK PICKS AFTER 2 HOURS | |
| BACK PICKS AFTER CALENDAR | N/C |
| | |
| COMMENTS | WIRE HAS TO RUN THROUGH WEFT STOP MOTION |
| NEW ENGLAND ELECTRIC WIRE CORPORATION | LISBON, NH |

FIG.5A

| | |
|---|---|
| BAR 1 | 4 ENDS 1/150 SD |
| BAR 2 | 19 ENDS 1680 LYCRA |
| BAR 3 | 2 ENDS 1/150 SD |
| BAR 4 | 3 ENDS NE 12544 TR TINNED COPPER WIRE |
| BAR 5 | |
| BAR 6 | |
| BAR 7 | |
| BAR 8 | |
| WARPS | 12 ENDS 1/150 SD |
| | |
| NEEDLES – WIDTH | 19–1 1/4" |
| STRETCH AT KNITTER | 110+/–10% |
| STRETCH AFTER 2 HOURS | |
| STRETCH AFTER CALENDAR | N/C |
| FRONT PICKS | 19 |
| BACK PICKS AT KNITTER | 40 |
| BACK PICKS AFTER 2 HOURS | |
| BACK PICKS AFTER CALENDAR | N/C |
| | |
| COMMENTS | WIRE HAS TO RUN THROUGH WEFT STOP MOTION TO REDUCE VIBRATION |

NEW ENGLAND ELECTRIC WIRE CORPORATION   LISBON, NH

FIG.6A

COMPOSITE ELASTIC AND WIRE FABRIC FOR PHYSIOLOGICAL MONITORING APPAREL

FIELD OF THE INVENTION

The present invention relates generally to elastic fabrics used in the construction of garments, and, more particularly, to elastic fabrics having conductive wiring affixed to the fabric for use in garments intended for physiological monitoring of prescribed body functions.

BACKGROUND OF THE INVENTION

As the administration of health care services has shifted from hospital-based or office-based care to home-based or patient-borne self care, strides have been made in the development of devices and garments for monitoring physiological signs, while allowing patients to maintain lifestyles as normal as practical. Thus, traditional invasive-type devices could not be used for such purposes. To overcome the inherent risks in these invasive monitoring devices, non-invasive devices have been developed for adaptation in conventional garments or have been worn on some part of the body; e.g., wristwatch-like.

The development of these new non-invasive devices has paralleled advances in systems for monitoring vital signs and for communicating this information, particularly when abnormal, directly to the patient as well as to health care providers through a variety of means, including infrared links. However, these devices heretofore have not provided the level of reliability and accuracy necessary for monitoring certain health conditions or vital signs.

There is known in the art a non-invasive physiological monitoring system comprising a garment in the form of a shirt, multiple inductive plethysmographic sensors attached to and supported by the garment, a transmitter attached to the garment and to the multiple sensors for transmitting signals from the garment, and a processor unit remote from the garment for receiving the signals and sending messages back to the patient. The sensors comprise ends of conductive wire attached to the garment at the measurement points for the physiological signs. The sensors have been attached to the garment in a prescribed curved configuration, desirably sinusoidal, so that as the body expands and contracts the sinusoidal pattern changes with a corresponding change in inductance in the wires. Inductance is the input into the transmitter that is subsequently translated into a physiological reading. However, the manner in which these conductive wires have heretofore been attached to the shirt have led to less than optimal accuracy and reliability as the relative locations of the wires in the garments have shifted or the attachment points have degraded. For example, conductive wires have been adhered to paper substrates and subsequently attached on or within sleeves of the garment adapted for their placement. While these constructions have advanced the art of physiological monitoring, they have not proven satisfactory for consistent, long-term performance; e.g., paper substrates wear and tear and conductive wires lose their designed configuration for proper monitoring.

SUMMARY OF THE INVENTION

The present invention relates to a fabric for use in apparel of the type used for physiological monitoring of prescribed human body functions. In the preferred embodiment, this fabric includes an elongated band of elastic material that is stretchable in the longitudinal direction, and at least one conductive wire incorporated into or onto the elastic fabric band in a prescribed curved configuration. As the fabric stretches, the curvature of the conductive wire changes. As this occurs, the inductance of the conductive wire varies, and is measured and processed by an attached or monitoring unit. An object of the present invention is to provide a fabric and conductive wire construction that will provide reliable, consistent, and long-term performance.

The elongated band of elastic material may be formed in any of the conventional ways for forming elastic fabric. These include warp knitting, weft knitting, weaving, braiding, or forming in a non-woven construction. Warp knitting is preferable because conventional crochet machines are adaptable to form bands of elastic having narrow widths. The elastic band of the present invention is desirably ¾ to I V$_2$ inches wide, but may be as narrow as ¼ inch. The elastomeric material used to form the elongated band of elastic material is desirably Lycra® or Spandex® because of their superior elasticity. Additionally, because these man-made filaments are not abrasive or irritating to the skin, they are quite suitable for applications where the elastomeric material is in direct contact with the skin. However, for most applications, natural extruded filaments of latex may be used for the elastomeric material.

In forming the elastic band on a conventional crochet machine, such as a machine manufactured by Jacob Müller as Model RD3-8/420 (Jakob Müller of America, Inc., Charlotte, N.C.), the elastic filaments form the warp beams in a longitudinal direction. The fill, or weft, may be formed from a variety of yarns including, not limited to, single-ply, 150 denier polyester; 2-ply, 70 denier nylon; 2-ply, 100 denier polyester; and, 2-ply, 150 denier polyester.

At least one conductive wire is incorporated with the elastic fabric. As used herein, "incorporated" means that the conductive wiring is either intermeshed with the elastic fabric structure or operably affixed to at least one face of the elastic fabric. Copper wire in the 27 American wire gauge ("AWG") to 28 AWG range has been found most suitable for knitting on crochet machines; however, as those skilled in the art will appreciate, other sizes may be used depending upon the particular machine and machine setup being employed. One such suitable wire is NE 12544 TR Tinned Copper Wire, available from New England Electric Wire Corporation of Lisbon, New Hampshire. The wire may be either braided or stranded and coated or uncoated as long as it may be shaped and incorporated into the fabric in a prescribed curved configuration, preferably sinusoidal.

For monitoring certain physiological functions where a higher degree of sensitivity and accuracy is required, multiple wires are interconnected in a garment to form a single continuous conductive circuit that encircles the monitored area a number of times corresponding to the number of wires. Where multiple conductive wires are required, they may be affixed to a single elastic fabric band so that they are substantially in parallel relation or are in substantially overlapped relation. Once the elastic fabric band is incorporated into a garment, the wires may be interconnected.

While knitting the conductive wire into the fabric structure at the time of forming the elastic band is most efficient and economical, the conductive wire may be sewn to at least one surface of an elastic fabric band in a separate manufacturing step subsequent to formation of the elastic fabric band. Accordingly, this subsequent attachment may be performed either manually or automatically.

Alternatively, the conductive wire and fabric structure may be formed in a braided construction. Formed in this manner, a number of groupings of elastomeric fibers or filaments may be intertwined by braiding. One of the groupings of fibers or filaments will carry a conductive wire, coated or uncoated. The size and number of elastomeric fibers or filaments in each grouping, in combination with the number of groupings, will determine the size of the sinusoidal pattern of the wire. This braiding technique results in a more compact construction that will stretch and contract, providing an output signal to a monitoring unit.

As a further alternative, the conductive wire and fabric structure may be formed in a~non-woven construction. At least one conductive wire, shaped in a sinusoidal arrangement, is placed in a long narrow mold. Manufactured filaments; e.g., polyester, nylon, etc., are extruded and crisscrossed over at least one side of the shaped wire to form a web or mesh-like overlay. Finally, a film of elastomeric material is extruded to encapsulate one or both surfaces of the wire and web layers. When cooled and dried, this structure will stretch and contract to deliver a satisfactory, reliable output signal.

These and other aspects of the present invention will become apparent to those skilled in the art after a reading of the following description of the preferred embodiment when considered with the drawings.

DETAILED DESCRIPTION OF THE PREFERRED EMBODIMENTS

Figure 1:
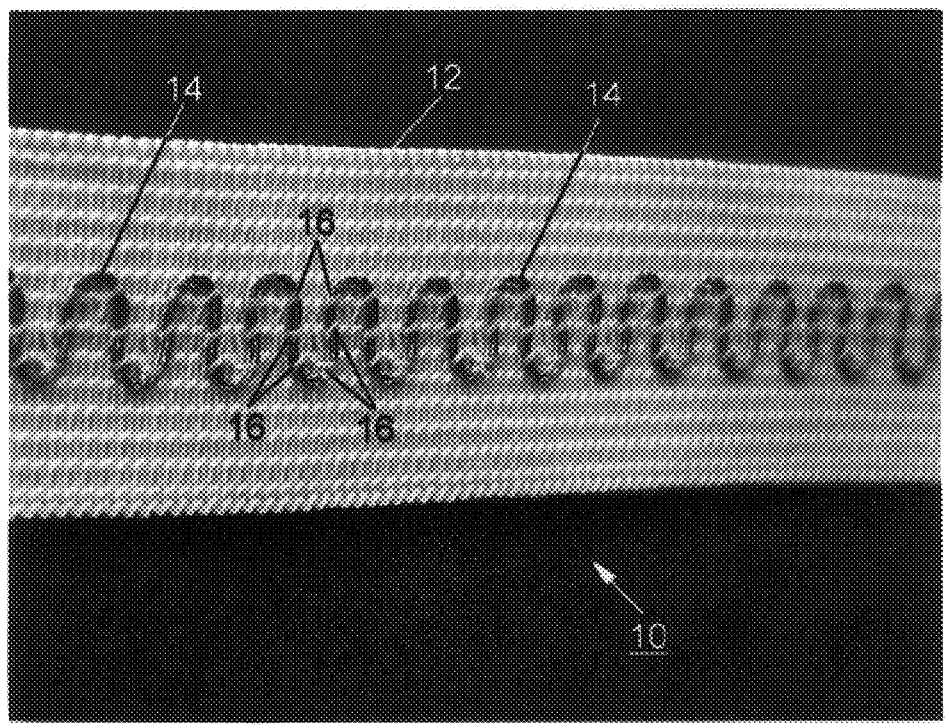
FIG. 1 is a perspective view of a composite fabric constructed according to the present invention with a single uncoated conductive wire.
Figure 3:
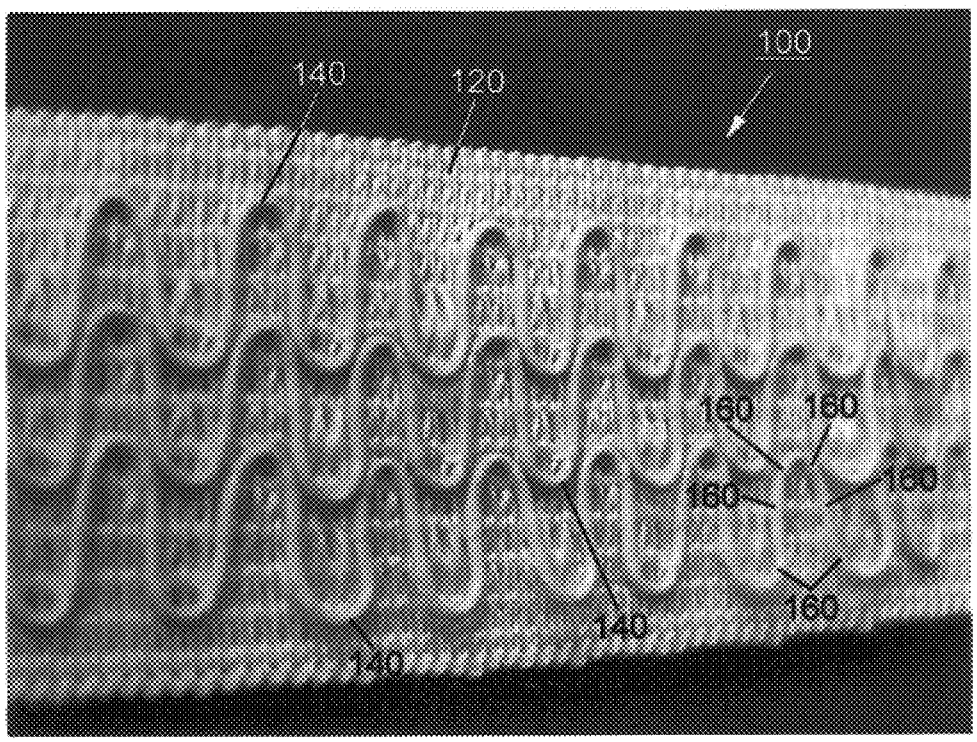
FIG. 3 is a perspective view of a composite fabric constructed according to the present invention with a plurality of parallel-coated conductive wires.

Referring now to FIG. 1, there is illustrated a fabric construction, shown generally as 10, for use in apparel of the type used for monitoring prescribed physiological functions. Fabric 10 generally comprises an elongated band of elastic material 12 and at least one conductive wire 14 affixed to the elastic fabric band. As used herein, the term "affixed" means knitted in, sewn onto, or intermeshed with the fabric construction. FIG. 3 further demonstrates a fabric construction 100 used for monitoring applications that require multiple conductive wires 140. Where multiple conductive wires 140 are required, they may be affixed to the band of elastic material 120 in substantially parallel fashion, or may be overlapped The elongated band of elastic 12, 120 may be formed in any of the conventional ways for forming elastic fabrics including warp knitting, weft knitting, or weaving. Warp knitting on a crochet machine is particularly suited to the present invention since this type of machine is easily adaptable to producing elastic fabric bands having narrow widths. One such machine is an 8-bar crochet machine manufactured by Jacob Müller as Model RD3-8/420 (8-bar, 420mm).

The band of elastic 12, 120 may vary in width from less than one inch to ten inches, but a width of approximately one inch has been found satisfactory for constructions having one to three conductive wires 14, 140. For an elastic band 12, 120 stretchable in the longitudinal direction, the filaments comprising the warp are elastomeric. Spandex® or Lycra®, available from DuPont, have proven most suitable in the present invention. These manmade strands have superior elasticity and have been found to be less abrasive and less irritating to bare skin than natural strands. However, for those applications in which direct contact between the skin and the fabric 10, 100 is not contemplated, extruded natural latex strands will provide satisfactory elasticity.

Since elasticity is required only in the warp, or longitudinal, direction, a variety of fill, or weft, yarns may be used to complete the formation of fabric 10, 100. While single ply, 150 denier polyester is quite suitable, other suitable yarns including 2 ply, 70 denier nylon; 2 ply, 100 denier nylon; and, 2 ply, 150 denier polyester, have been found suitable. However, other yarns, formed of natural and man-made materials, as well as other deniers, may also be suitably used.

The wire used to create the conductive fabric must have conductive properties, but otherwise may be formed in a number of ways. It may be stranded, braided, cotton covered, Teflon coated, uncoated, or any variety of other configurations. The curved shape, preferably sinusoidal, that is created with the wire is ideally configured to have a height of approximately ⅜" from base to peak, with the sinusoidal curve repeating approximately each ⅜". This has proven appropriate for the inductance process. However, the height and repeatability of the sinusoidal shape could vary considerably and still perform the required functions. The main consideration is that the conductive wire pattern expands and contracts without hindrance when placed in the appropriate locations about the body.

Conductive wire 14, 140 may be operably affixed to the elastic band 12, 120 by sewing in a separate operation subsequent to formation of the band 12, 120, but it has been found most efficient and cost effective to form the entire composite elastic and wire fabric integrally in the same knitting operation."Operably affixed" means that the shape of the conductive wire pattern will change proportionally as the elastic band 12, 120 is stretched. As shown in FIGS. 1 and 3, conductive wire 14, or conductive wires 140 have been stitched onto the face of elastic bands 12, 120 in a sinusoidal pattern during the knitting operation. While other curve-like configurations may be acceptable, a sinusoidal pattern formed in a warp-knitting process is more easily formed and provides the optimal geometry for the intended application. Critical to the wire configuration is the presence of rounded curves with no sharp turns.

Conductive wires 14, 140 may vary in size and construction depending upon the capability of the machine used to form fabric 10, 100. Copper wire constructions in the 27 AWG to 28 AWG range have proven most desirable for fabric 10, 100 knitted on crochet machines. For example, 27 AWG 12-5-44 cotton braided, 27 AWG 12-5-44-braided wire, or 28 AWG 40/44 tinned copper wire have all proven acceptable. Conductive wire 14, 140 may be either coated or uncoated, with the choice for coating being based on aesthetic, as opposed to functional, reasons. A polyvinyl chloride (PVC) coating is both conventional and acceptable for the present invention. Also, a fabric cover such as cotton may be used as an outer covering for the conductive wire 14, 140.

Figure 2:
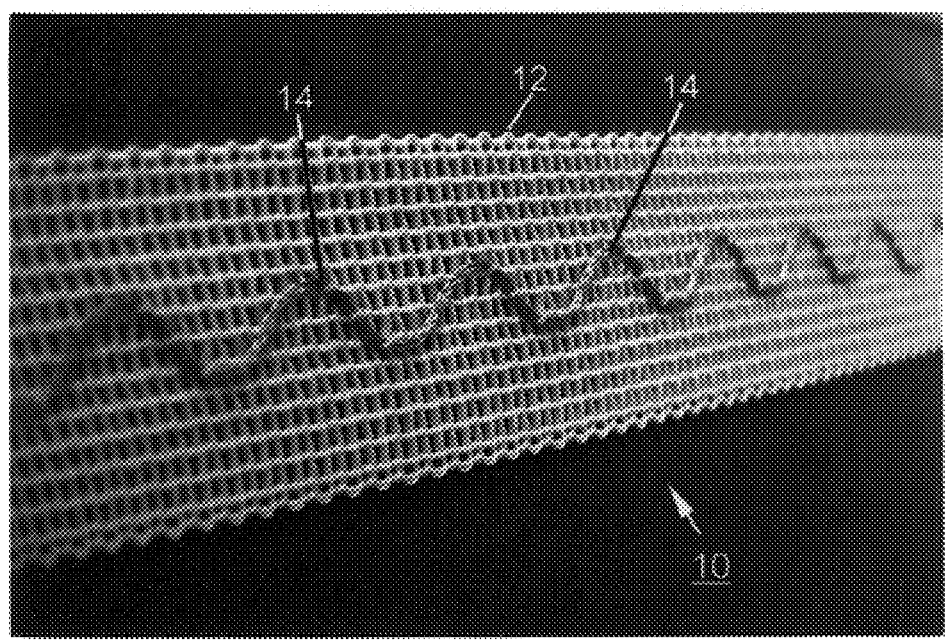
FIG. 2 is a perspective view of the composite fabric of FIG. 1 with the fabric stretched in the longitudinal direction.
Figure 4:
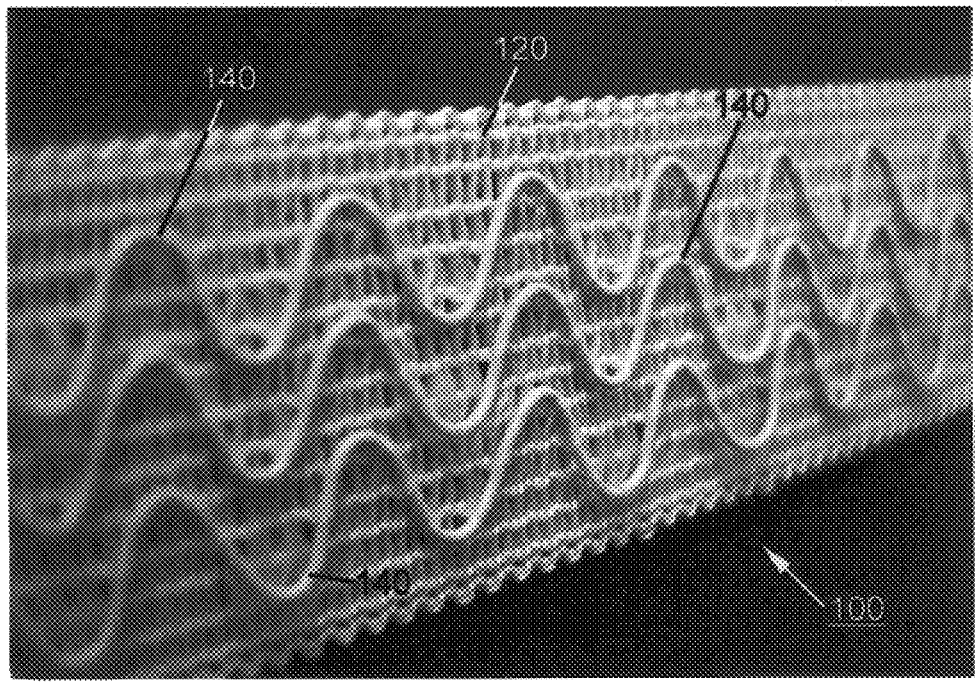
FIG. 4 is a perspective view of the composite fabric of FIG. 3 with the fabric stretched in the longitudinal direction.

To keep from bending or knotting the conductive wire 14, 140, it has been found that a knitting pattern movement allowing the wire 14, 140 to remain between knitting needles for two consecutive stitches provides an optimal construction that permits the wire 14, 140 to stretch uniformly as elastic band 12, 120 stretches. FIGS. 2 and 4 best illustrate how wire 14, 140 uniformly changes shape as elastic band 12, 120 is stretched in a longitudinal direction. This knitting pattern allows a "softer" bending of the wire 14, 140 by not moving the wire 14, 140 with each stitch.

In forming a knitted fabric structure, the crochet machine draws each individual warp yarn through a guide mounted on a guide bar. Tension is applied to stretch the warp yarns.

Movements of the guide bar (lapping) cause each yarn to lap around a needle. After the yarns are lapped, the needle bar on the machine is moved so as to cause loops to be formed simultaneously at all needles, resulting in a whole knitted course. A yarn inlay is next drawn across the lower warp yarns. As the guide bar is displaced sideways (also known in the art as "to shog") by one or more needles, the upper and lower warp yarns change places before the next cycle produces another course. The shogging of the guide bar determines the structure of the fabric.

Figure 5B:
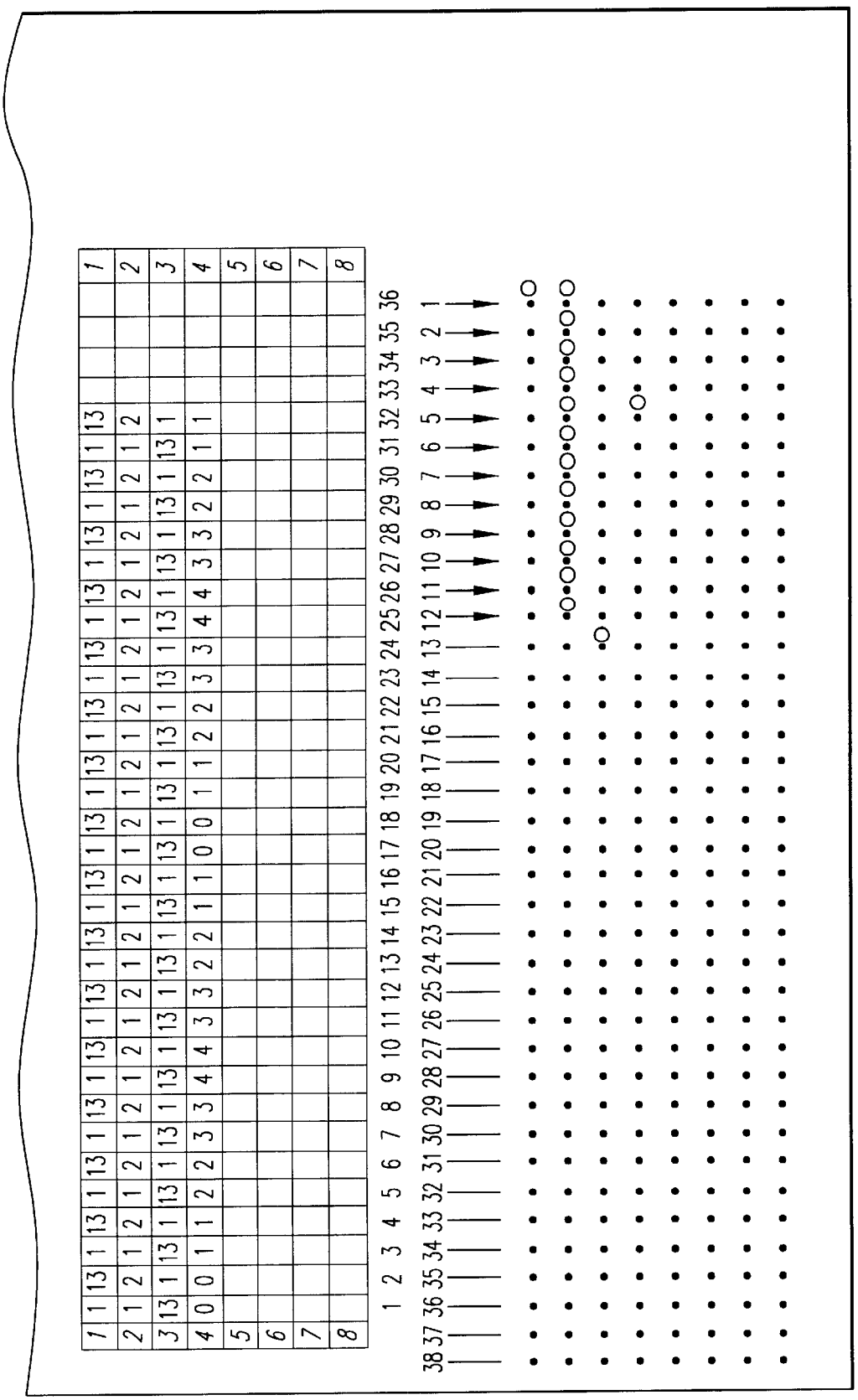
FIG. 5 shows the setup specifications for a single wire construction.

For a fabric and wire construction employing a single wire, the machine is initially set up for two warp beams with a total of 15 Lycra® warp yarns/filaments and 1 nylon or polyester weft inlay yarn. FIG. 5 provides the setup specifications for this construction. Odd numbered warp yarns are on one beam, while even numbered yarns are on the other beam. In addition to this, a beam of 1 conductive wire is setup and fed through a yarn guide that is directed by a special bar. The bar controls the movement of the guide back and forth across the fabric as the fabric is being formed. The appropriate guide for this formation holds the conductive wire in the position (along the 3rd or 4th warp yarn from the right) for 2 stitches, then shogs left over the next warp yarn (position 1) where it holds for 2 stitches. The bar then causes the guide to shog left again, to position 2 for 2 stitches, and so on until it reaches the 3 or 4 warp yarn on the left side of the fabric setup. At that point it begins shogging to the right in the same manner until it returns to position 0 to start the process over. This 0-0-1-1-2-2-3-3-4-4-3-3-2-2-1-1 pattern allows the creation of a sinusoidal shape that has both an amplitude and peak of approximately ⅜".

Figure 6B:
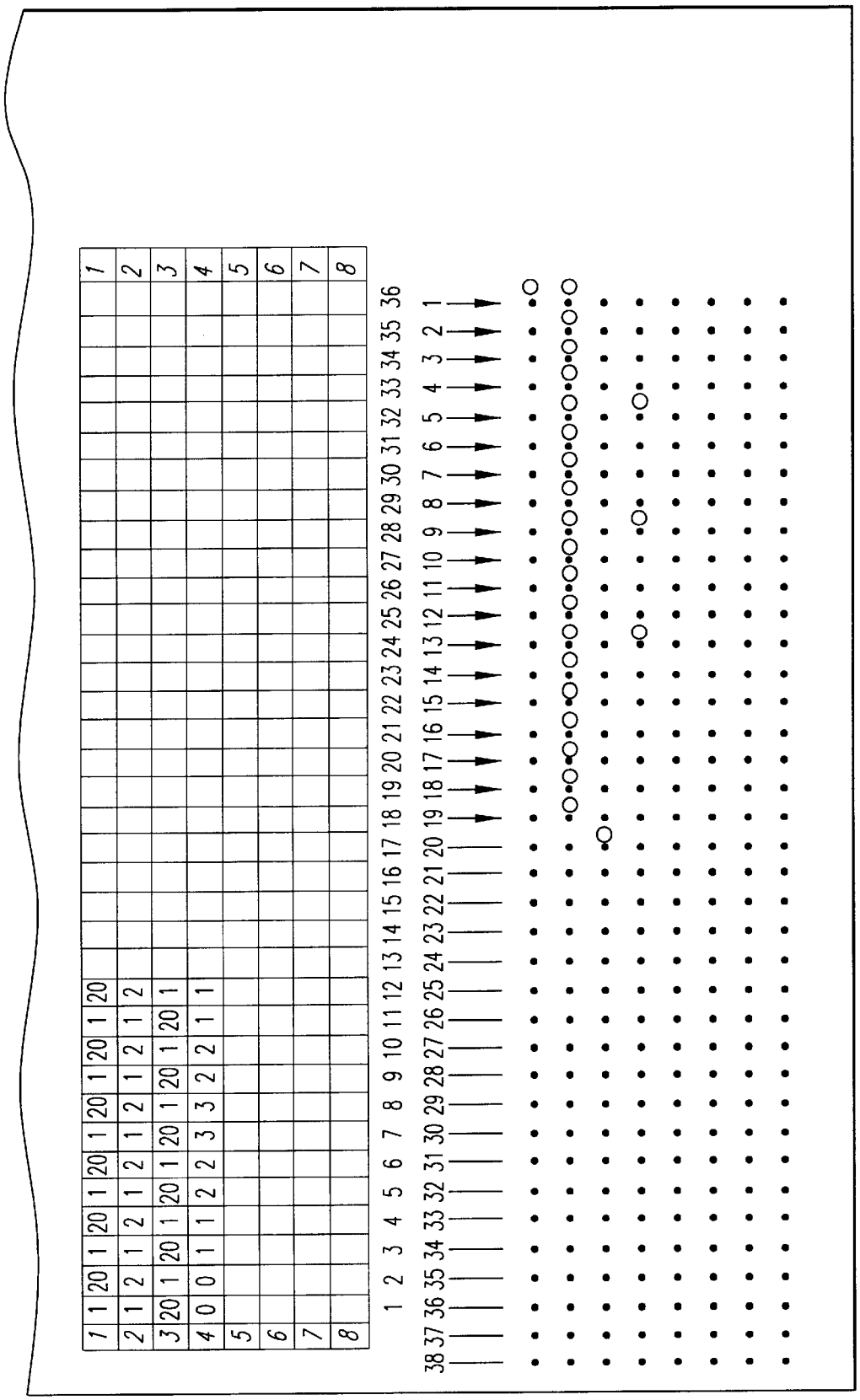
FIG. 6 shows the setup specifications for a three-wire construction.

For a fabric and wire construction employing three conductive wires, the warp machine is setup with 17 or more Lycra® warp yarns and 1 nylon or polyester weft inlay yarn. FIG. 6 provides the setup specifications for this construction. In addition to this, a beam of 3 conductive wires is setup and fed through 3 separate yarn guides that are directed by the same special bar as is used for the single conductive wire. The bar controls the movement of the 3 guides back and forth across the fabric as the fabric is being formed. The appropriate guide for this formation holds the conductive wires in the 0 position (wire~1 along the $_3$rd yarn, wire #2 along the $_4$th yarn, and wire #3 along the $_5$th yarn from the right) for 2 stitches. The control bar then shogs the three wire guides left over to the next warp yarn (position I) where it holds for 2 stitches. The bar then causes the guides to shog left again, to position 2 for 2 stitches, and so on until it reaches the 3rd or 4th warp yarn on the left side of the fabric setup. At that point it begins shogging to the right in the same manner until it returns to position 0 to start the process over. This 0-0-1-1-2-2-3-3-4-4-3-3-2-2-1-1 pattern allows the creation of three parallel sinusoidal shapes that have both an amplitude and peak of ⅜".

[???? please check these braiding specifications ????]

Figure 7:
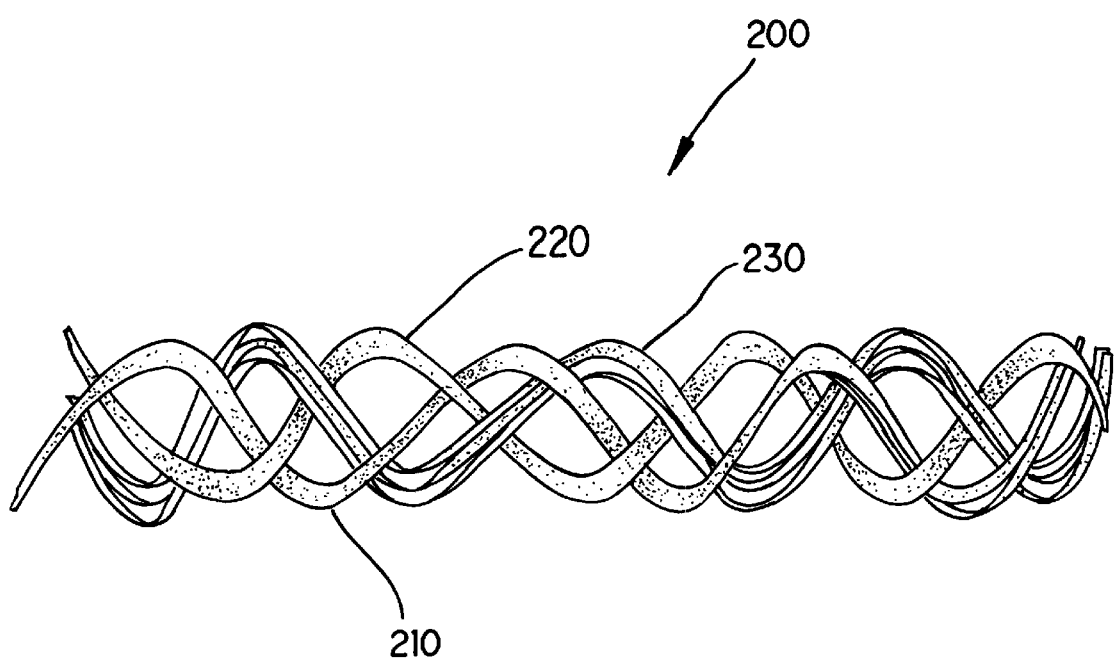
FIG. 7 is a schematic illustration of a braided fabric incorporating one conductive wire.

As shown in FIG. 7, another embodiment of the present invention, shown generally in an open and enlarged view as 200, is a composite fabric and conductive wire band formed by braiding. Formed in this manner, at least three groupings 210, 220, and 230 of elastomeric fiber may be intertwined by knitting on a warp knitting machine with weft insertion (such as Jacob Müller model Raschelina RD3-8/420, or an equivalent model) in a conventional manner known in the art. [???? correct ????] One of the groupings of fibers 230 will carry a conductive wire, coated or uncoated. For example, one grouping may consist of ¹⁄₁₅₀ textured polyester or equivalent with an elastomer of Spandex® or rubber or equivalent. These may be arranged as 6 ends of ¹⁄₁₅₀ polyester weft yarn, 23 ends of ¹⁄₁₅₀ polyester warp yarn, 23 ends of 1120 Spandex® warp yarn, and 1 or more ends of conductive wire in a warp direction. [???? correct ????] The size and number of elastomeric fibers in each grouping, in combination with the number of groupings, will determine the size of the sinusoidal pattern of the wire. This braiding technique results in a more compact construction that will stretch and contract, providing an output signal to a monitoring unit for interpretation. Although three groupings are shown in FIG. 5, groupings of 5, 7, 9 or more may also be intertwined; depending upon the capability of the machine.

Those skilled in the art will appreciate that there are other warp to form constructions that will function as desired. For example, the conductive wire and fabric structure may be formed in a non-woven embodiment. At least one conductive wire, shaped in a sinusoidal arrangement is placed in a long narrow mold. Manufactured filaments; e.g., polyester, nylon, etc., are extruded and crisscrossed over at least one side of the shaped wire to form a web or mesh-like overlay. Finally, a film of elastomeric fiber is extruded to encapsulate one or both surfaces of the wire and web layers. When cooled and dried, this structure will stretch and contract to deliver a satisfactory, reliable output signal.

Figure 8:
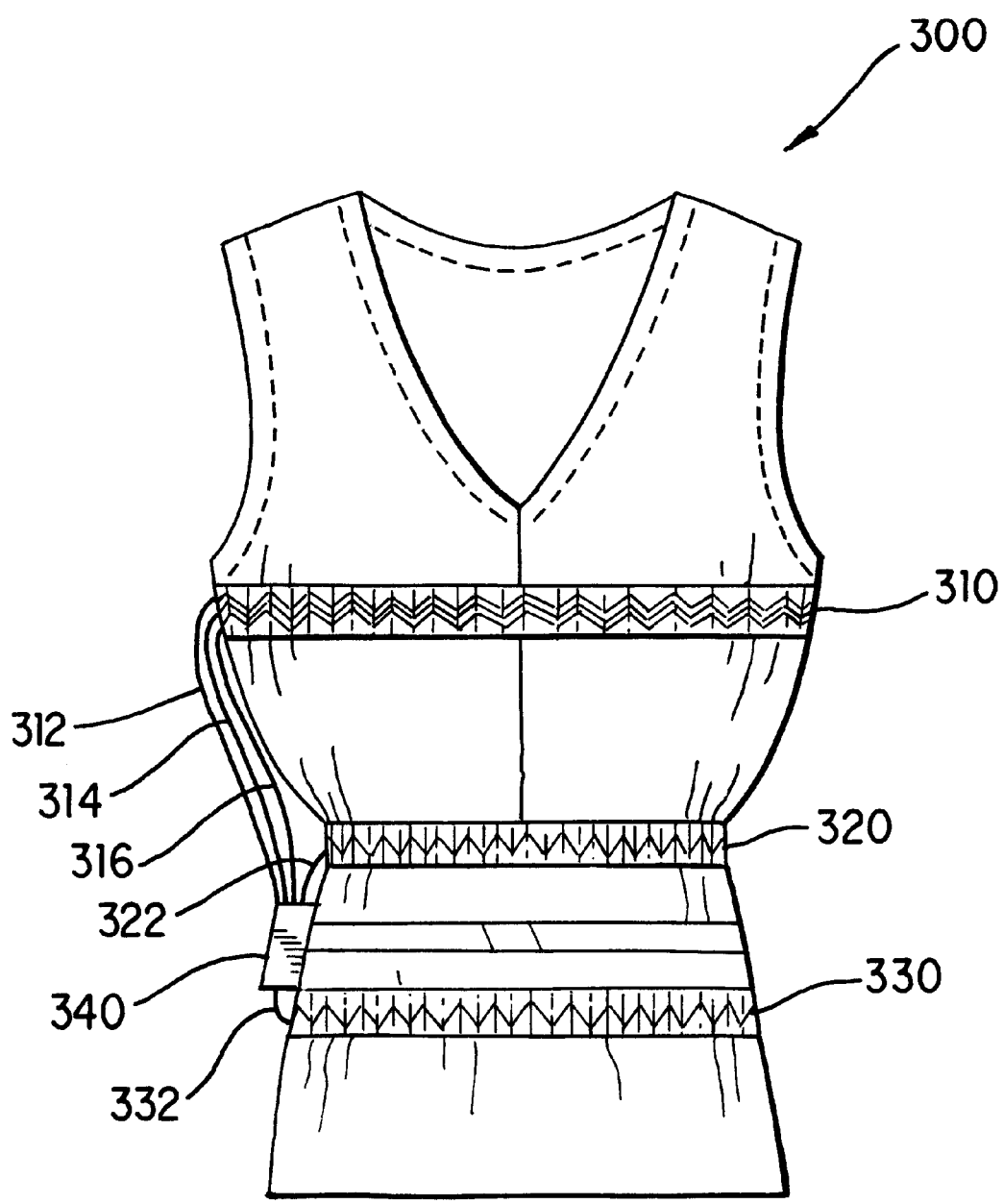
FIG. 8 is a front view of a garment constructed according to the present invention incorporating the composite fabric.

Turning to FIG. 8, a garment 300 in the form of a shirt is shown with composite fabric and wire fabric bands 310, 320, and 330 environmentally depicted at representative locations on garment 300. Band 310 illustrates how a 3-wire construction is used in regions such as the wearer's chest, while 320 and 330 are single wire constructions. The conductive wires, shown as 312, 314, 316, 322, and 332, provide outputs to an attached monitoring unit 340. Although shown loosely connected, the conductive wires may otherwise be attached or affixed to garment 300.

The fabric and wire bands may be attached to garments in any of several ways. They may be inserted into tunnels or casings created within the garments, including the sleeves and/or collar bands. They may be sewn onto the inside or outside surface of the garment in a stretched shape so that the garment contracts after sewing. Also, they may be attached to the garment with a series of strategically placed "belt loops" on the inside or the outside of the garment. Monitoring unit 340 may be fitted into a pocket in the garment, clipped onto the garment or other item of clothing, or otherwise conveniently carried by a wearer of the garment.

Figure 9A:
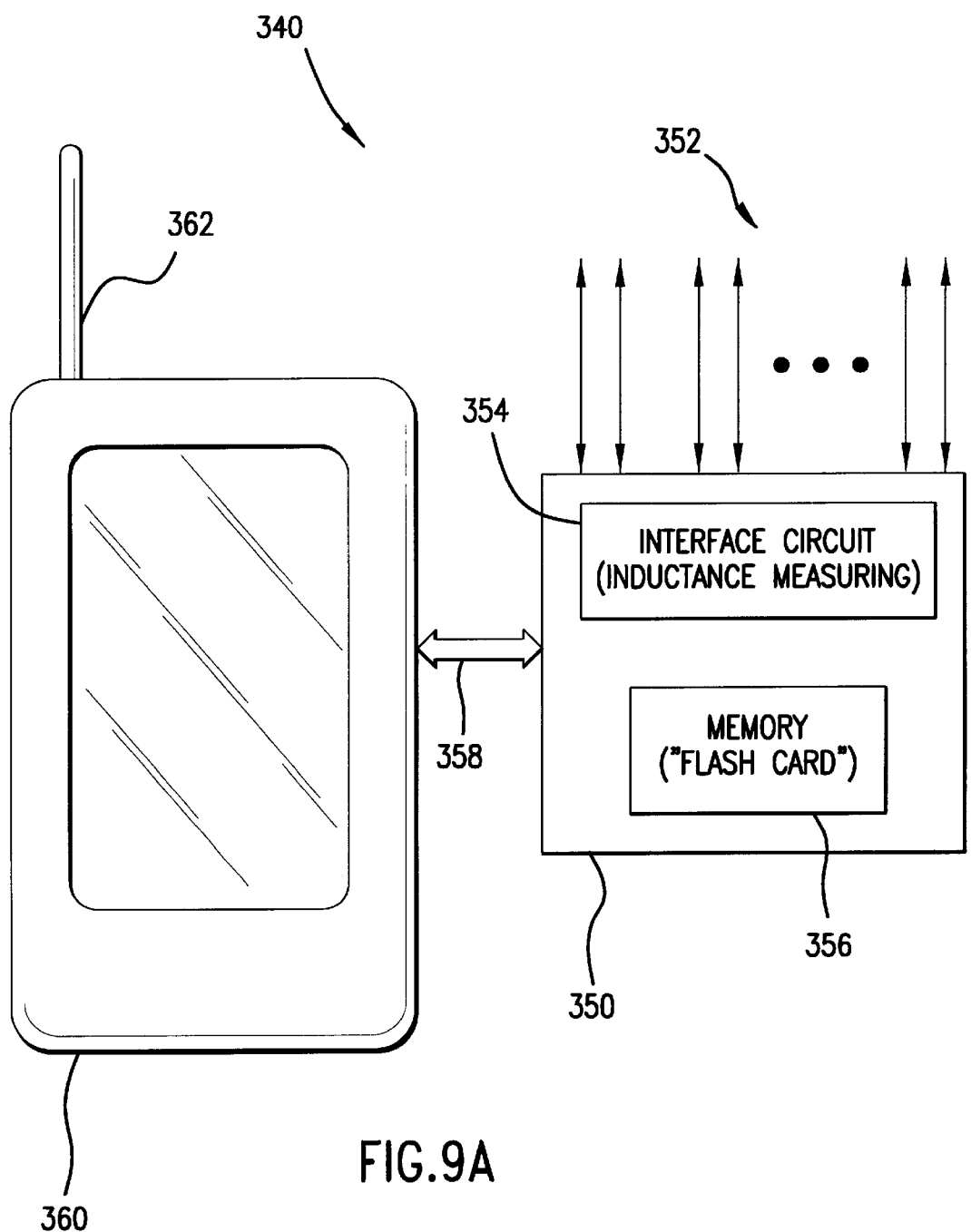
FIGS. 9A–B are block diagrams describing the physiological monitoring unit of the present invention.

FIG. 9A illustrates a preferred embodiment of a programmable monitoring unit adapted to monitor a garment, such as garment 300, which produces inductive signals in response to changes in a wearer's physiological functions. The preferred embodiment generally includes interface unit 350 and user device 360. The interface unit includes interface circuit 354, which measures in well known manners the inductance of one or more pairs of monitoring leads 352, and memory 356, which stores monitoring results. Preferably, memory 356 is configured as a removable card, such as the widely used flash memory cards. The user device is preferably a standard handheld device, such as a Handspring VISOR, configured for coupling to interface unit 352 by means of a plug, socket, receptacle, or so forth, generally indicated as interface 358, and loaded with program instructions which cause it to perform the processing described below. Optionally, the user interface device is configured for remote communications, such as by a wireless link indicated by antenna 362.

Figure 9B:
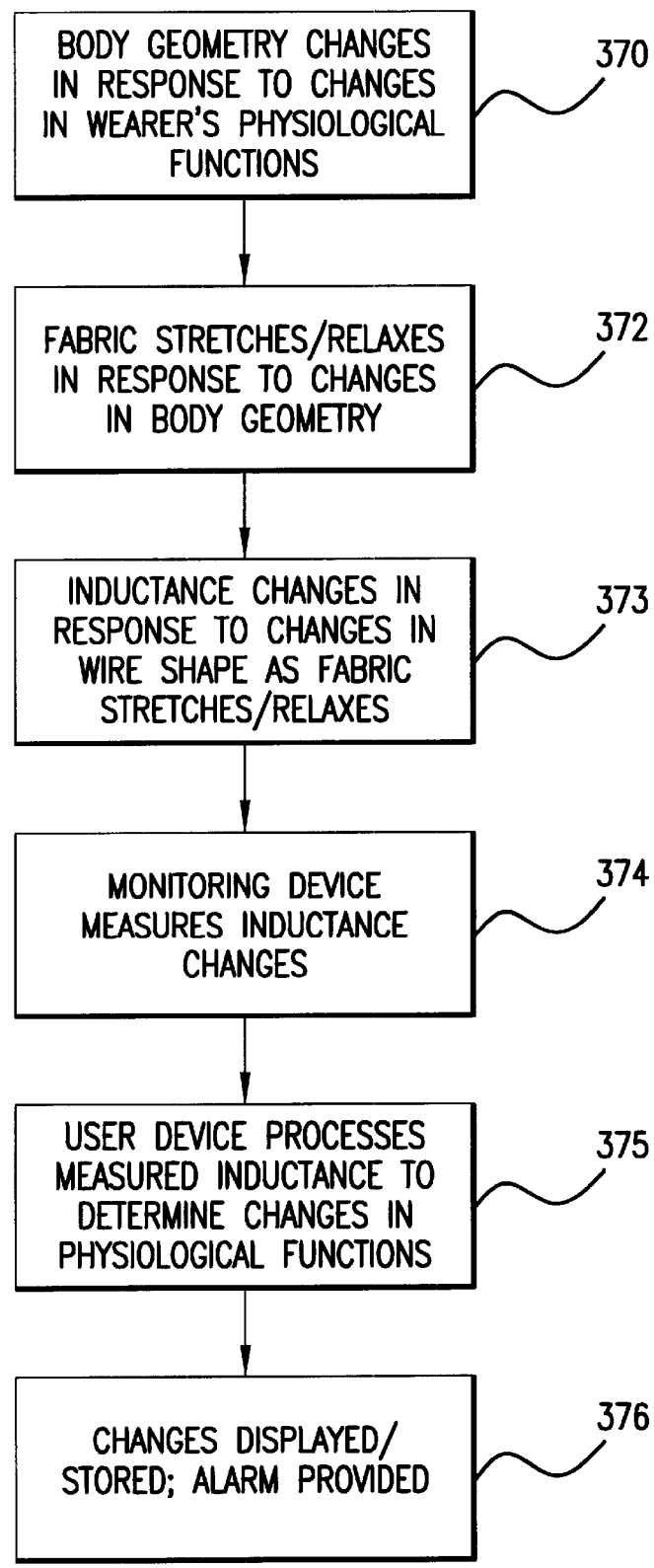

FIG. 9B depicts the operation of a physiological monitoring system comprising a garment with composite fabric construction and a monitoring unit. Since the fabric constructions are incorporated into the garment such that they are snugly fitted around the wearer's body, as the wearer's physiological functions change, as when breathing in and out, the geometry of the body changes (370); i.e., expands and contracts. This causes the fabric to stretch and contract (372) in response to changes in the body geometry. The stretching and contracting causes the curvature, or sinusoidal shape, of the affixed conductive wires to change accordingly. This change in shape of the conductive wires causes the inductance the individual wires to vary (373). The monitoring unit measures the varying inductance (374) and processes it (375) in order to obtain the wearer's physiological indications from the measured inductance, to store the monitoring results in memory 356, and optionally, to transmit the results remotely. Finally, the monitoring results may be displayed (376) to the wearer and alarms generated if necessary.

Alternatively, in a simpler embodiment, the monitoring results can be directly transmitted to a remote processing location, without processing in the vicinity of the wearer. This embodiment, although less preferred for an ambulatory user, may be more preferred when the user's motion is confined, for example, to a bed.

Certain modifications and improvements will occur to those skilled in the art upon a reading of the foregoing description. It should be understood that all such modifications and improvements, while not discussed in detail hereinabove, are properly within the scope of the following claims.

What is claimed is:

1. A composite fabric construction for use in apparel of the type used for monitoring physiological parameters comprising:
    (a) an elongated band of elastic material which is stretchable in the longitudinal direction; and
    (b) at least one conductive wire incorporated with said elastic fabric band in a prescribed curved pattern extending along said longitudinal direction, wherein stretching or contracting of the fabric changes the curved pattern of the wire, and thus changes the inductance of the wire.

2. The composite fabric of claim 1 wherein said conductive wire is intermeshed within said elastic fabric structure of said elastic band.

3. The composite fabric of claim 1 wherein said elastic band is a knitted fabric.

4. The composite fabric of claim 1 wherein said prescribed curved pattern is substantially sinusoidal.

5. The composite fabric of claim 1 wherein said curved pattern has an amplitude of about ⅜ inches and a repeatability about every ⅜ inches when in an unstretched condition.

6. A garment of the type for use in physiological monitoring of prescribed body functions comprising a fabric construction, wherein the fabric construction includes:
    (a) an elongated band of elastic material which is stretchable in the longitudinal direction and which is incorporated into the garment in such a manner as to expand and contract responsive to the body function; and
    (b) at least one conductive wire affixed to said elastic fabric band in a substantially sinusoidal pattern extending along said longitudinal directions, wherein stretching or contracting of the fabric changes the curved pattern of the wire, and thus changes the inductance of the wire.

7. A composite fabric construction for use in apparel of the type used for monitoring physiological parameters comprising:
    (a) an elongated band or cord of elastic material which is stretchable in the longitudinal direction; and
    (b) at least one conductive wire formed with said elastic fabric band or cord in a prescribed curved pattern extending along said longitudinal direction, wherein stretching or contracting of the fabric changes the curved pattern of the wire, and thus changes the inductance of the wire.

8. A garment of the type for use in physiological monitoring of prescribed body functions comprising a fabric construction, wherein the fabric construction includes:
    (a) an elongated band or cord of elastic material which is stretchable in the longitudinal direction and which is incorporated into the garment in such a manner as to expand and contract responsive to the body function; and
    (b) at least one conductive wire formed with said elastic fabric band or cord in a prescribed curved pattern extending along said longitudinal direction, wherein stretching or contracting of the fabric changes the curved pattern of the wire, and thus changes the inductance of the wire.

9. A system for physiological monitoring of prescribed body functions comprising
    (a) a monitoring unit for measuring and processing an inductance signal;
    (b) a garment of the type worn over the torso;
    (c) an elongated band or cord of elastic material which is stretchable in the longitudinal direction and which is incorporated into the garment in such a manner as to expand and contract responsive to the body function; and
    (d) at least one conductive wire formed with said elastic fabric band or cord in a prescribed curved pattern extending along said longitudinal direction, wherein stretching or contracting of the fabric changes the curved pattern of the wire and thus the inductance of the wire, said monitoring unit being responsive to the inductance of the wire.

* * * * *